(12) United States Patent
Jacobs et al.

(10) Patent No.: US 6,454,729 B1
(45) Date of Patent: Sep. 24, 2002

(54) DATA PROCESSING METHOD FOR INTERPRETATION OF MEASUREMENTS OF GROWTH

(75) Inventors: Joan R. Jacobs, Worthington, OH (US); Olga Kuznetsova, Edison, NJ (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/853,218

(22) Filed: May 11, 2001

(Under 37 CFR 1.47)

(51) Int. Cl.$^7$ ................................................. A61B 5/00
(52) U.S. Cl. ....................................................... 600/587
(58) Field of Search ................................ 600/300, 587, 600/595

(56) References Cited

U.S. PATENT DOCUMENTS

| | | | |
|---|---|---|---|
| 5,005,143 A | 4/1991 | Altschuler et al. | |
| 5,057,992 A | 10/1991 | Traiger | |

OTHER PUBLICATIONS

Abstract: Analysis of short–term growth of premature infants during the first days of life assessed by mini–knemometry, A. Keller, M. Hermanussen, CH Vogtmann, J. Burmeister, E. Keller, Leipzig, Aschauhof, Germany XP 008000355.

Computer Program for Fitting the Logistic and the Gompertz Function of Growth Data, E. Marubini and L.F. Resele, Computer Programs in Biomedicine 2 (1971) 16–23 XP 008000339.

Non–linear Curve Fitting and the True method of Least Squares, Richard William Farebroher, The Statistician (1998) 47, Part 1, pp. 137–147 XP 008000341.

Growth Models: A Generalized Approach, K A P Menon and B. Bowonder, Journal of Scientific and Industrial Research, vol. 39, Mar. 1980, pp. 132–137.

Individual Growth of Stature of Japanese, Takao Shohoji and Hiroshi Sasaki, Growth, 1987, 51, 432–450 XP 008000360.

Abstract: Use of a Gompertz Curve to Describe patterns of Early Growth in Term and Preterm Infants, Zhang, Use of American J. of Human Biology vol. 10, No. 1, 1998 (#165).

Abstract: Growth of Preterm Infants Fed Nutrient Enriched or Term Formula After Hospital Discharge, Carver, Pediatric Academic Societies & American Academy of Pediatrics Joint Mtg 2000.

Application of the Gompertz Curve to the Observed pattern of Growth in Length of 48 Individual Boys and Girls During the Adolescent Cycle of Growth, Deming, Human Biology vol. 29 83–122, 0018–7143 1957.

Fitting a Gompertz Curve to Adolescent Standing Height Growth Data, Pasternack et al, Fitting Adolescent Growth Data Chapter 35 pp. 559–577, 1976.

(List continued on next page.)

Primary Examiner—Max Hindenburg
(74) Attorney, Agent, or Firm—Thomas D. Brainard

(57) ABSTRACT

The invention comprises methods and devices that are developed using subject modeling functions of the form $f_{a,b,c}(t)=a \exp(b(1-\exp(-ct)))$. These methods and device are particularly useful in the study and interpretation of subject growth. The function parameters are calculated to give optimal curve fit to subject data, such as anthropometric growth date like weight, length, and head circumference as a function of an age measure, t. Preferably the subject is an infant and the age measure, t, is gestation-adjusted age. The fitted functions can be used to estimate subject sizes at a different, predetermined age, and the estimated sizes may be subjected to statistical analysis to determine which factors, if any, have affected growth of the infant.

20 Claims, 1 Drawing Sheet

OTHER PUBLICATIONS

Dynamics of Relative Growth, Laird, GROWTH, 1965 39 pp. 349–263.

Postnatal Growth of Birds and Mammals, Laird, GROWTH, 1966 30 pp. 349–363.

Evolution of the Human Growth Curve, Laird, GROWTH, 1967 31 pp. 345–355.

A Modified Growth Curve Model and Its Application to Clinical Studies, Weissfeld et al, Austral. J. Statist., 34 (2), 1992, 161–168.

Growth Changes: Measuring the Effect of an Intervention, Heimendinger et al, Evaluation Rev, vol. 7 issue 1, 1983 80–95.

Comparison of Two Longitudinal Growth Models for Preschool Children, Berkey, Biometrics 38 221–234, Mar. 1982.

A Lifetime Asymptotic Growth Curve for Human Height, Jolicoeur et al, Biometrics 44 995–1003, Dec. 1998.

Mathematics and the Growth of Organisms—Some Historical Impressions, Sandland, 1983, pp. 11–30.

A nonlinear model of growth in the first year of life, Giani et al, Acta Paediatr 85:7–13 1996.

The Illusion of Catch–up Growth in Premature Infants, Karaiski et al, AJDC, vol. 141 May 1987 520–526.

The Model for Describing Normal and Abnormal Growth in Early Childhood, Berkey et al, Human Biology, Dec. 1987, vol. 59 No. 6 973–987.

The preterm small–for–gestational age infant: A two–year follow–up study, Vohr et al, Am. J. Obstet. Gynecol, Feb. 15, 1979, vol. 133 No. 4 pp. 425–431.

Inference for the Association Between Coefficients in a Multivariate Growth Curve Model, Zucker et al, Biometrics 51, 413–424 Jun. 1995.

Food Consumption and Growth of Normal Infants Fed Milk–Based Fomulas, Fomon et al, ACTA Peadiatrica Sandinavia Supplement 223, 1971, 1–23.

What is a normal rate of weight gain in infancy?, Wright et al, ACTA Paediatr 3:351–6 1994.

Nutrient intake and growth performance of older infants fed human milk, Stuff et al, The Journal of Pediatrics, Dec. 1989, 959–968.

Adequacy of energy intake among breast–fed infants in the DARLING study: Relationships to growth velocity, morbidity, and activity levels, Dewey et al, Energy intake among breast–fed infants, vol. 119 No. 4, 538–547.

Growth in Infancy and Childhood in Girls with Turner's Syndrome, Kalberg et al, ACTA Paediatr Scand 80:1158–1165, 1991.

Monthly Growth Status from a Longitudinal Study of Canadian Infants, Guo et al, Canadian Journal of Public Heath, vol. 81 May/Jun. 1990 215–221.

Cross sectional stature and weight reference curves for the UK, 1990 Freeman et al, Archives of Disease in Childhood 1995; 73:17–24.

Body mass index reference curves for the UK, 1990, Cole et al, Archives of Disease in Childhood 1995; 73:25–39.

Individual Growth Curves and Longitudinal Growth Charts between 0 and 3 years, Milani et al, ACTA Paediatr Scand Suppl 350:95–104 1989.

Growth Charts for Both Cross–Sectional and Longitudinal Data, Cole, Statistics in Medicine vol. 13, 2477–2492 1984.

Incremental Growth Charts, Roche et al, Am. J. Clin. Nutri. 33: Sep. 1980, pp. 2041–2051.

Reference data on gains in weight and length during the first two years of life, Guo et al, J. of Pediatrics Sep. 1991 vol. 119 No. 3 pp. 355–362.

Reference data for head circumference and 1 month increments from 1 to 12 months of age, Guo et al, J of Pediatrics Sep. 1988 vol. 113, No. 3 pp. 490–494.

PC Program for Estimating Polynomial Growth, Velocity and Acceleration Curves When Subjects May Have Missing Data, Schneiderman et al, Int J Biomed Comput 33 (1993) 249–265.

A GAUSS Program for Computing an Index of Tracking From Longitudinal Observations, Schneiderman et al, Am. J. of Human Biology 2:475–490 (1990).

Weight–for–length model in newborn Swedish infants, Niklasson et al, ACTA Paediatr 82:333–9, 1993.

Converting Tanner—Whitehouse reference tricep and subscapular skinfold measurements to stand deviation scores, Davies et al, European J. of Clin. Nutrition (1993) 47:559–566.

Indicators for monitoring the Growth of Peruvian Infants: Weight and Length Gain vs Attained Weight and Length, Piwoz et al, Am J of Public Health, 1994, 84:1132–1138.

The predictive value of childhood body mass index values for overweight at age 35 y, Guo et al, Am J Clin Nutr 1994: 59:810–9.

Determining Growth Faltering With a Tracking Score, Frongillo et al, Am J of Human Biology 2:491–501 (1990).

Neonatal morphometric indices of fetal growth: analysis of observer variabilty, Change et al, Early Human Development 35 (1993) 37–43.

Clustering on the Basis of Longitudinal Data, Eschneiderman et al, Comput Biol Med vol. 23 No. 5 pp. 399–406 1993.

Modeling of Nonlinear Growth Curve on Series of Correlated Count Data Measured at Unequally Spaced Times: A Fully Likelihood Based Approach, Lambert, Biometrics 52, 50–55 Mar. 1996.

On Predication of Future Observation in Growth Curve Model, Tian et al, Statistics in Medicine, vol. 13 2205–2217 (1994).

Mathematical models for the study of individual growth patterns, Hauspie et al, Epidem et Sante Publ, 1989 37, 461–476.

Unequally Spaced Longitudinal Data with AR (1) Serial Correlation, Jones et al, Biometrics 47, 161–175 Mar. 1991.

Methods for Comparing Groups of Growth Curves When Patterns of Observation Times Vary Among Subjects, DeWitt et al, GROWTH, 1984, 48, 187–191.

Human Stature: Which Growth Model?, Jolicoeur et al, Growth Development & Aging 1991, 55 129–132.

Growth status and growth rates of a varied sample of low birth weight, preterm infants: A longitudinal cohort from birth to three years of age, Casey et al, The J of Pediatrics vol. 119 No. 4 Oct. 1991 599–605.

Postnatal Growth in Infants Born Between 700 and 1,500g, Cooke et al, J. of Pediatric Gastroenterology and Nutrition 16:130–135 1993.

Enhancing the Outcomes of Low–Birth–Weight, Premature Infants, A. Multisite, Randomized Trail, JAMA Jun. 13, 1990 vol. 263 No. 22 3035–3042.

Growth Dynamics of Low–birth–weight Infants, Brandt et al, ACTA Paediatr Scand Suppl, 319:38–47 1985.

Fitting Mixture Models to Birth Weight Data: A Case Study, Oja et al, Biometrics 47 883–897, Sep. 1991.

Comparison of the Gompertz and Weibull Functions as Descriptors for Human Mortality Distributions and Their Intersections, Jucket et al, Mechanisms of Aging and Development, 69 (1993) 1–31.

Linear growth retardation in relation to the three phases of growth, Karlberg et al, European Journal of Clinica Nutrition (1994) 48 (Suppl 1) S25–S44.

Modeling Lactation Using An Inverse Polynomial in a Multilevel Statistical Model, Drewett et al, Statistics in Medicine, vol. 12 949–954 (1993).

Quantitative Genetic Analysis of IQ Development in Young Children: Multivariate Multiple Regression with Orthogonal Polynomials, Waldman et al, Behavior Genetics, vol. 22, No. 2 1992.

Using Growth modeling to Examine Systematic Differences in Growth: An Example of Change in the Functioning of Families at Risk of Maladaptive Parenting, Child Abuse, or Neglect, Wellett et al, J of Consulting and Clin Psychology 1991, vol. 59 No. 1 38–47.

A Generalized Growth Curve Procedure for the Analysis of Incomplete Longitudinal Data, Vonesh et al, SUGI 11: Proceedings of the Eleventh Annual SAS Users Group International Conference, Atlanta, GA, Feb. 9–12, 1986, Cary, NC: SAS Institute; 1986:889–894.

Inference from the Incomplete Longitudinal Design: A collect of SAS Marcos, Rochon et al, SUGI 11: Proceedings of the Eleventh Annual SAS Users Group International Conference, Atlanta, GA, Feb. 9–12, 1986, Cary, NC: SAS Institute; 1986:883–888.

Short term grown: rhythms, chaos, or noise?, Wales, Department of Paediatrics, University of Sheffield, Children's Hospital, Arch–Dis–Child. 1994 Jul.; 71(1):84–9.

A review of two different approaches for the analysis of growth data using longitudinal mixed linear models: Comparing hierarchial linear regression (ML3, HLM) and repeated measures designs with structured covariance matrices (BMDP5V), van der Leeden et al, Computational Statistics & Data Analysis, 1996, V21, N5 (May), P 583–605.

On the Nature of the Function Expressive of the Law of Human Mortality; and on a New Mode of Determining the Value of the Life Contingencies. In a Letter to Francis Baily, London; W. Nicol; 1825.

DATA PROCESSING METHOD FOR INTERPRETATION OF MEASUREMENTS OF GROWTH

FIELD OF THE INVENTION

The present invention relates to improved statistical methods making use of estimated or approximated data and, more particularly, to the study of subject growth rates and the statistical treatment of subject growth data, particularly infant size data such as weight, length and head circumference.

BACKGROUND

Data is collected and analyzed to determine the effects of various influences on growth, particularly infant growth. Such influences may include genetic factors, environmental factors or interventions such as nutritional or medical treatment For example, many studies have been conducted to determine how differences in infant formula composition affect growth of an infant. Data must generally be interpreted using statistical methods to separate and distinguish "apparent" effects that are due to random, uncontrolled variability from "true" effects that result from differences in the formulas tested in the study.

One source of uncontrolled variability that influences the precision and reliability of growth data is the timing at which growth measurements are made. Typically, a researcher wants to compare study outcomes (e.g. size parameters such as weight, length and head circumference, or mental development parameters, such as Bayley's) as a function of time, to determine what relationship, if any, exists between the factor or intervention being tested and the subject's growth rate. Study outcomes, such as subject sizes, would ideally be measured at predetermined ages selected by the researcher, for example at precisely 2, 4 and 6 months. In practice however, the outcome measurements may not be made at precisely the targeted time. For example, in infant growth studies, the infant-subjects often are not brought in for measurements at the precise time predetermined by the researcher, so subject growth data is collected at irregular times. Because infants grow and change very quickly, even a few days difference between the predetermined target time for a measurement and the actual time at which the measurement is made is a source of uncontrolled variability that can significantly affect the interpretation of the data. This variability can reduce the usefulness of the data and reduce the precision of the statistical comparisons.

To address this problem of time-variability of measurements in infants, it has been suggested that an infant growth model be used. A number of growth models have been proposed in the literature. Count, E., 15 *Human Biology* 1–32 (1943) discloses a size modeling function, including one of the form $f_{a,b,c}(t)=a+b\,t+c\,\log(t+1)$. Guo, et al., 119 *J. Pediatr.* 334–362 (1991) describe a function of the form $f_{a,b,c}(t)=a+b\,\log(t+1)+c\,\sqrt{t+1}$. Karlberg et al., 48 (*Suppl.* 1) *European Journal of Clinical Nutrition* S25–S44 (1994) teach a model of the form $f_{a,b,c}(t)=a+b\,(1-\exp(-cx))$. These and other infant growth models are reviewed by Peerson, et al., in an article titled Use of Growth Models to Describe Patterns of Length, Weight, and Head Circumference among Breast-Fed and Formula-Fed Infants: The Darling Study, *Human Biology*, 65(4):611–626, 1993. These known infant growth models have limited usefulness, however, and are generally inapplicable to preterm infant growth data.

In addition, a Gompertz function has been applied to growth modeling in the adolescent by Pasternack and Shohoji in *Essays in Probability and Statistics* (Ikeda, Sadao, et. al. eds), Fitting a Gompertz Curve to Adolescent Standing Height Growth Data, (Chapter 35, pp. 559–577, Shinko Tsusho, Tokyo, 1976), and by Deming, *Human Biology*, 29:83–122 (1957). A Gompertz function has also been used to model growth of whole organisms, both pre- and post-natal, as well as various organs and parts of whole organisms in a series of 1960's papers by A. K. Laird. See, for example, Laird, Dynamic of Relative Growth, *Growth* 29, 249–363 (1965); Laird, Postnatal growth of birds and mammals, *Growth* 30:349–363 (1966); and Laird, Evolution of the human growth curve, *Growth*, 31:345–355 (1967).

A portion of applicants' own work was published in abstract form: Zhang et al, Use of a Gompertz curve to describe patterns of early growth in term and preterm infants (Abstr. #165) *Amer. J. of Human Biology*, 10:1 pp 139–140, 1998. To applicants' knowledge, however, the use of such Gompertz functions has not previously been applied to evaluate studies in which time is the independent variable and for which the data may not conform precisely to the desired times. To applicants' knowledge, the function has not previously been used to predict or approximate data points for a time common to multiple subjects, followed by the comparison of such estimated data for evaluation of the intervention of the clinical trial. Weissfeld and Kshirsagar, *Austral. J. Statist.*, 34(2):161–168 (1992) describe a modified use of a growth modeling function (not Gompertz) to adapt it to a same-patient-multiple-treatments format in order to test certain hypotheses about the treatments.

SUMMARY OF THE INVENTION

In one aspect, the invention provides a method of interpreting results from a study, said method comprising the steps of:

obtaining measured size data for each of two or more subjects regarding the subjects' sizes as a function of an independent variable, t, that corresponds to a measure of the subjects' ages, wherein t for at least one subject differs from t for at least one other subject;

determining for each of the subjects a set of values for the three parameters a, b, and c of a three parameter size modeling function defined by $f_{a,b,c}(t)=a\exp(b(1-\exp(-t)))$, to provide an optimal fit of the size modeling function to the data regarding the subject's size as a function of t;

estimating for each of the subjects, using said size modeling function and said set of determined values for the parameters, sizes for the subject at a particular age, which particular age is the same for all of the subjects; and comparing the estimated sizes to interpret the study results.

Preferably the optimal fit is obtained by minimizing the least squares error function. The age variable may be chronological age and, in an infant growth study—especially a preterm infant growth study, the age variable is preferably gestation-adjusted age. Comparing is a broad term that encompasses both simple comparisons and more complicated statistical analyses.

In another aspect, the invention provides a method of conducting a study, wherein the results are interpreted in accordance with the method described above.

In yet another aspect, the invention provides a device comprising:

memory means encoded with or adapted to receive instructions, said instructions capable of directing a computer provided with measured outcome data regarding a subject size as a function of an age, t, to calculate values for three parameters, a, b, and, c of a three parameter subject size modeling function defined by $f_{a,b,c}(t)=a \exp(b(1-\exp(-ct)))$; such that the size modeling function with the calculated parameter values gives an optimal fit of the function to the data;

instructions to use the calculated values for parameters a, b, and c in the size modeling function to generate estimated data for each subject at a common predetermined age that is different from t for at least one subject; and output means for presenting the estimated data.

In a preferred embodiment, the optimal fit is a least squares fit.

Another aspect of the invention provides a method of processing data for improved interpretation, said method comprising the steps of:

obtaining measured outcome data for a plurality of test subjects at times, $t_i$, corresponding to a measure of time, wherein $t_i$ for at least one subject differs from $t_i$ for at least one other subject;

determining for each subject a set of values for the three parameters a, b, and c of a three parameter modeling function defined by $f_{a,b,c}(t)=a \exp(b(1-\exp(-ct)))$ that relate outcome data to an independent time variable t, to provide an optimal fit of the modeling function to the measured outcome data for each subject over all $t_i$;

estimating outcome data for at least one of the subjects, using said modeling function and said the determined set of parameter values, for a particular time that is different from $t_i$ at which the outcome data was measured; and comparing the estimated outcome data from the at least one subject with estimated or measured outcome data from at least one other subject to interpret the results.

In this aspect, it is preferable that the outcome data be a measure of growth, including but not limited to anthropometric growth outcomes like weight, stature/length or head circumference. It is also preferable that the estimated outcome data be estimated for multiple, if not all the subjects; that the independent time variable is gestation-adjusted age; and that a computer processing means is used for some or all of the steps.

In a further aspect, the invention provides a process applied to data regarding a measure of subject size as a function of an independent variable t, corresponding to subject age, comprising the steps of: entering the data into a computer programmed to calculate values for three parameters, a, b, and, c in a three parameter subject size modeling function defined by $f_{a,b,c}(t)=a \exp(b(1-\exp(-ct)))$, wherein the computer is programmed to calculate the parameter values such that the modeling function with the calculated parameter values gives an optimal fit of the function to the data.

In a further aspect, the invention provides a method applied to data regarding a measure of subject size as a function of an independent variable corresponding to age, t, comprising the steps of: selecting a three parameter size modeling function defined by $f_{a,b,c}(t)=a \exp(b(1-\exp(-ct)))$; determining values for the three parameters a, b, and c to provide an optimal fit of the size modeling function to the subject size data; and recording the values for the three parameters, a, b, and c.

In each of the aspects described above, preferred embodiments include the following features: the optimal fit is a least squares fit; the parameter values are determined with the aid of a computer or similar processing instrument; and the estimated data is recorded on computer readable media. Further, it is often preferable that the subject size outcome is selected from the group consisting of weight, length, and head circumference; and the measure of age is gestation-adjusted age.

DESCRIPTION OF THE INVENTION

Figure 1:
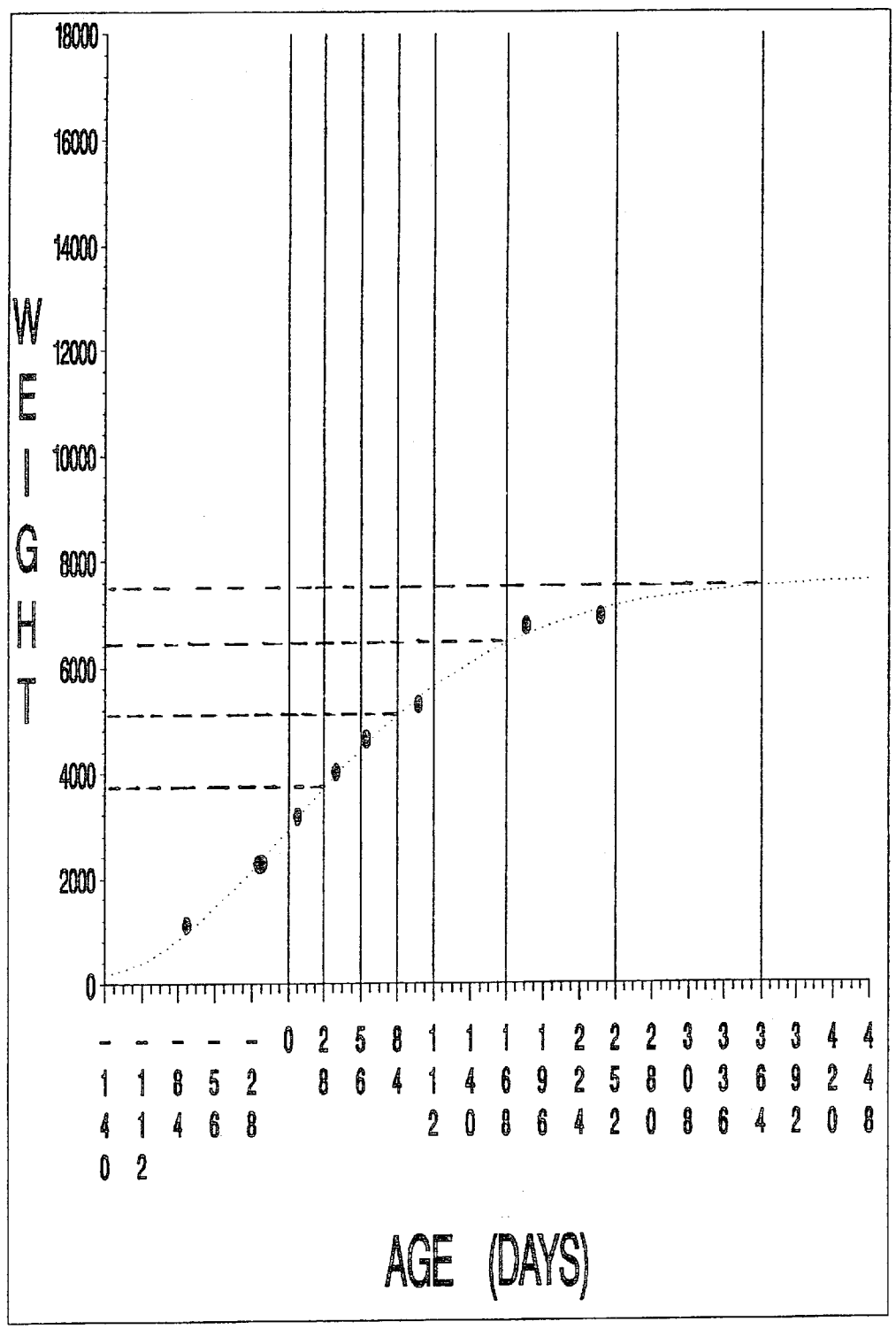
FIG. 1 is a graph illustrating weight (g) on the Y-axis versus gestation-adjusted age ("GAA") in days on the X-axis for subject No. 1802. This plot is a representative plot for infant growth; the data points are actual measured outcomes at the times noted. The vertical lines along the X-axis are the "target" times at which measurements were to be made according to the study protocol; note that the last projected data point is missing. The smooth curve dotted line is the "fitted function" of the form $f_{a,b,c}(t)=a \exp(b(1-\exp(-ct)))$, relating weight to GAA using the available data. The parameter values determined for this particular subject and curve are: a=2949.73; b=0.96276; and c=0.0099993. The "estimated" outcome weights used for statistical comparison are calculated from the function, but may be depicted graphically along the Y-axis at the points where the smooth curve intersects the vertical lines (dashed lines).

"Subjects" as used herein are the individuals involved in a study. They may be infants, especially preterm infants, or they may be older children or even adults in some embodiments. A particularly useful embodiment is described for clinical studies that involve modeling growth curves for preterm infants.

Among the first steps in designing a clinical study are selecting the "study variable" and the "outcomes" to be measured. The study variable is a factor that is allowed to vary between groups, while other factors remain controlled. Study variables may be divided into three broad groups: genetic factors, such as presence or absence of a particular gene or mutation; environmental factors, such as effects of smoking or sociological class; and interventions such as nutritional or medical treatments. In the case of a nutritional intervention, it is typically the formula, composition, regimen or protocol that one wishes to study to determine whether or not it has an impact on a specific outcome.

Also early on, one selects the "outcomes" that are to be measured during the study. An outcome may be any observable, measurable difference or change that can be assessed. In the case of infant nutritional studies, the outcome is typically anthropometric growth, but it may also be an outcome related to neurological or psychological development. Typical anthropometric or size measurements include weight, stature or length, and head circumference. Less frequently used anthropometric measurements include neck, chest, waist, torso or limb circumferences and/or lengths, skin fold thickness, body mass index, bone length or width and the like. The term "size" or size measurement as used herein refers to any of these anthropometric measures. In contrast, measurement outcomes associated with neurological or psychological development include Bayley's PDI and MDI Scales, MacArthur Language tests, Fagan Intelligence tests and the like. These are described in more detail in co-pending, co-owned application Ser. No. 09/821,368, filed Mar. 30, 2001 and incorporated herein by reference.

Outcome data, especially anthropometric growth data, including data for pre-term subjects, can be represented in terms of a three-parameter function having the form:

$$f_{a,b,c}(t) = a e^{b(1-e^{-ct})}$$

which is equivalent to $f_{a,b,c}(t)=a \exp(b(1-\exp(-ct)))$, in which "exp(x)" is the exponential function, e to the power of x; and a, b and c are parameters determined for each subject as discussed below. In this function, "$f_{a,b,c}(t)$" gives a subject size outcome as a function of a time measure ("t"). This functional form defines a family of functions that produce related curves. A second function, for example $g_{a',b',c'}(t)$, is in the same family as the function $f_{a,b,c}(t)$ if mapping functions x(a,b,c), y(a,b,c) and z(a,b,c) exist that provide a one-to-one mapping between the functions $f_{a,b,c}(t)$ and $g_{a',b',c'}(t)$ such that $g_{x(a,b,c), y(a,b,c), z(a,b,c)}(t) = f_{a,b,c}(t)$. A simple illustration of such a family of functions occurs when each parameter of the second function, $g_{a',b',c'}(t)$, is simply a multiple of the same parameter of the first function. In other words, the mapping function x(a,b,c) might be x=2a; the mapping function y(a,b,c) might be y=3b; and the mapping function z(a,b,c) might be z=4c. Another example of a second function in the same family is $g_{a',b',c'}(t)=(a')^3 \exp(b'(1-\exp(-c't)))$. In this case $x(a,b,c)=a^{(1/3)}$, y(a,b,c)=b, and z(a,b,c)=c. Other examples of members of a related family of functions are easily known to those skilled in the art of mathematics.

The independent variable, t or $t_i$, in the function represents a suitable measure of time. Chronological age (Current Date−Birth Date) is a suitable measure of time for some trials. But due to variability of gestation periods and the high growth rates in utero and as young infants, chronological age may not always be satisfactory for infant growth studies. A more suitable measure of time for infant studies is "conception age", typically defined as time since the mother's last menstrual period. Yet another suitable measure of time, especially for preterm infants, is "Gestation-adjusted age". Gestation-adjusted age, or "GAA" is what the infant's age would be if the infant had been born at full term of about 40 weeks. It may be calculated as:

GAA=(Current Date−Birth Date)+(Days Gestation−280)

For pre-term infants, GAA is negative until Days Gestation plus Chronological Age (Current Date−Birth Date) exceeds 280 days. Regardless of the time measurement used, the units, i.e. hours, days, weeks, months, etc., are interconvertible.

Preterm infants are defined as those infants born prior to about 37 weeks post-conception. While actual conception may not be precisely determinable, it can be approximated based on last menstrual cycle and/or on other objective estimates, such as early ultrasound assessments or clinical neonatal assessments such as Ballard's. The choice of which method to use in the event of discrepant results is often a matter of physician or institution preference.

The independent variable, t or $t_i$, may be measured at different time points for each subject. Indeed this is unavoidable in large studies due to the inability to force rigid compliance on physicians and busy caretakers with their own schedules to mind. Thus, in accordance with the invention, the t for at least one subject will differ from the t for at least one other subject near at least one predetermined target time T. More typically there are many, many such variances, both between different subjects and between a subject time t and the target time T, but the invention may still be useful when only one such variance exists.

During periods of rapid growth, such as infancy and adolescence, measuring outcomes at times not precisely aligned with the predetermined target time, T, introduces a source of uncontrolled variability and makes comparisons of the data more difficult as explained in the background. Thus, the present invention addresses this problem by providing a means to "normalize" or "process" the data to align it with the predetermined target time. Applicants discourage the use of "normalizing" terminology in this context so as to avoid confusion with the conventional statistical use of the term "normalizing". Thus, applicants will refer to the "processing" of data in the context of this invention.

The parameters "a", "b" and "c" are function parameters, which vary from subject to subject for each outcome measured. In a process known as "fitting" or "curve fitting", these parameters are determined empirically so as to provide an optimal fit of the function to the relevant outcome data. An "optimal fit" describes a function with parameters that minimizes the differences between the actual, empirical data and the function-generated or predicted data; in other words, an optimal fit minimizes "error functions." The most common error function used in statistics is known as the "least squares error" and is defined as the sum of the squares of the differences between the function values and the actual data. For example, if the outcome data are weights W(i), at ages T(i), for i=1 to n, n being the number of data points, the sum of the squares of the differences error function is given as:

$$\sum_{i=1}^{n}(W_{Ti} - f_{a,b,c}(Ti))^2$$

The selection of parameters a, b, and c that minimize this particular error function give an optimal fit that is called a least squares fit. Other error functions are known to those of ordinary skill in the art. For example, the error function could be the sum of the absolute values of the differences between the function values and the actual data. One skilled in the art can select the error function most suited to the particular facts, although the least squares error function is by far the most common in infant growth modeling.

Generally, it is preferable to determine or calculate the parameters from the data using a computer program that employs a standard numerical method. For example, computer instructions for carrying out a least squares fit of subject size data to a subject size modeling function can easily be prepared and stored in computer memory using commercially available software, such as the SAS® software (Cary, N.C.). The outcome data can also be entered into the computer and the results of the optimal fitting process can be stored in computer readable media or output to a monitor or printer.

Computer components useful in the present invention are not very different from personal computers, now ubiquitous in business and industry. Basically, the computer comprises a processing means, typically referred to as a CPU. The processing means receives, interprets, and executes the various sets of coded instructions. Accompanying the processing means are usually memory means, output means, input means and data storage means. Memory means, typically referred to as RAM or random access memory, is a location for storing, at least temporarily, data, calculations or other information. Output means are any devices that present information or data in a manner suitable for perception by human senses, typically sight; or by other machine-readable devices, such as a modem. Output means include, by way of example, monitors, printers, and speakers.

Similarly, input means are devices or interfaces that permit a user to provide data or instructional input the processing means. Keyboards, scanners, character recognition devices, mouse and other pointer devices (e.g. trackballs, pens, styli, "erasers", and thumb pads) microphones, joysticks, and the like are representative examples of input devices. Data storage means include various media on which the processing unit may store data, information or instructions. Data storage media is typically magnetically or optically encoded. Examples of data storage means include floppy diskettes, compact disks ("CDs"), so called "Zip" drives, hard drives, including networked storage drives, and the like. Computer processing means operate via a set of instructions coded in a manner so as to be understood by the computer, typically in binary fashion. Sets of instructions or "code" can operate on several levels (e.g. machine code, source code, application code), and may be "hard" coded into a particular device or "soft" coded. Soft coded instructions are commonly referred to as software.

Computer processing means may be employed in virtually any of the steps of the invention, but are particularly useful for the steps of determining the three parameters in such a manner as to produce an optimal fit; and for the steps of carrying out a statistical analysis.

Outcome data, such as subject size data, can be compared with greater precision and reliability using the size modeling function of the invention. Recall that the actual outcome data is often not measured precisely at the predetermined target time T, specified by the study protocol. The first step in such a comparison is to fit the size modeling function to the data for each subject. This process determines parameters a, b and c for each subject. It may be meaningful to compare the parameter values for one subject directly with the parameter values for a second subject if a function can be identified for which the parameters are themselves meaningful.

A more typical second step, however, is to use the fitted functions with determined parameters to produce estimated or approximated outcome data for each subject at one or more predetermined target times, T, for example, at 12 weeks gestation-adjusted age, that are the same for each subject. This method of data processing serves to adjust or align the outcome data to a common target time T, which facilitates the comparison of data among subjects.

Interpolation and extrapolation are two specific forms of estimated data. Interpolation involves the estimation of data for at least one time point that occurs between two actual measured data time points. The interpolated data point is bounded by two actual measured data points. Extrapolation, on the other hand, involves the estimation of data for at least one time point that extends beyond any actual measured data time points, and may be in the forward or future direction, or in the rearward or past direction. In general, interpolation is considered safer and is more accepted than extrapolation, but extrapolation is tolerated and accepted when the distance from actual data is not too significant and when the fit of the curve to the data is quite good.

Formal comparison of the results of an intervention in a clinical trial usually involves testing one or more specific null hypotheses against one or more specified alternatives for the statistical analysis. This often requires the identification of an appropriate model with well-defined parameters (such as the mean and variance) for a known, usually normal, distribution. In the analysis of infant growth it is desirable to obtain repeated measures of the variables of interest, such as weight, at fixed times, such as 8, 14, 28, 56, 84, 112 days, etc. A desirable analysis follows the repeated measures longitudinal design of the clinical trial or study and facilitates drawing inferences about changes over the interval as well at the individual times. The statistical test compares estimates for each of the interventions based on the group means at each of the timepoints. If there is a systematic time-shift in the data collection for one intervention, the group mean estimates used may be biased. The use of the present invention to allow individual estimates at precisely the desired timepoints leads to more comparable group mean estimates for use in the statistical analysis by eliminating or reducing any time-shift bias in data collection.

The most apparent utility of the present invention is in the interpretation of data generated by growth studies, such as infant growth clinicals. In the specific case of a nutritional product growth clinical, a statistical analysis is performed on the estimated growth data (instead of or in addition to the raw growth data) in order more precisely to evaluate the treatment intervention. The intervention in this case is typically a difference in the formula composition the subjects have been fed.

A second possible utility is in the assessment of wound care interventions, such as for example the success or not of a treatment for burns or skin ulcers. Since wounds close and heal via the mechanism of cell growth and proliferation, an inverse application of the invention may be used to assess the treatment interventions. Actual measurements of wound size are often used to track healing and the timing of each measurement may not be consistent across all patients in a trial. Thus, inventive method can be employed to process and "align" the data to a time point that is common to all subjects. Additional methods of using the invention and the invention's advantages will become apparent to one of ordinary skill in the art.

The following example is illustrative of the invention, but the scope for which protection is sought is set forth in the appended claims. Additionally, a description of statistical analysis terminology is found in the Background section of the example but this applies generally to the invention and not just the illustrative example.

EXAMPLE

A Study of the Effects of Formula on Growth

Part A—Background

A multisite, randomized, double-blind, parallel design study was conducted to determine how a particular formula composition impacts the growth of preterm infants. Subjects were followed from just prior to hospital discharge until 12 months gestation-adjusted age ("GAA"). Subjects were randomly assigned to a feeding group, to be fed either a standard term infant formula (Similac With Iron® or "SWI") or an enriched formulation (NeoSure® or "NEO"). Outcome growth data consisted of a measurement of each subject's weight, length and head circumference taken on the day on which formula feeding began (study day 1) and at the target times of approximately 0 (term), 1, 4, 8, 12, 16, 24, 36 and 52 weeks GAA. The study was divided in two stages with a preliminary analysis of the data through 16 weeks (Stage 1), followed by a final analysis after 52 weeks (Stage 2).

For each subject, an individually fitted curve of the form $f_{a,b,c}(t)=a\exp(b(1-\exp(-ct)))$ was generated for each outcome following both Stage 1 and Stage 2. The parameters a, b, and c, used to fit the curves were calculated using the non-linear least squares procedure of the statistical methods software SAS® v6.09e (PROC NLIN). Starting parameter values were determined based on previous work with similar data (a=400–3000, b=0.5–1.7, c=0.001–0.02); the modified Gauss-Newton iterative method available in the SAS software PROC NLIN was specified to maximize the number of subjects for which the subroutine converged. Subjects for whom the model did not converge generally failed to have a sufficient number of post-discharge observations and were dropped from the data set for purposes of modeling.

Estimated data were generated by using the fitted functions to estimate the subject weight, subject length, and subject head circumference at the precise target times called for by the study, i.e. 0, 1, 4, 8, 12, ,16, 24 ,36 and 52 weeks GAA.

A single subject, subject No. 1802, was selected as representative and weight data for this subject is presented in FIG. 1 and in Table 1.

Thus, a feeding group interaction with birthweight group (such as is seen with head circumference below), is represented as feeding group*birthweight group. It is important to test for interactions to gain confidence that an observed significant difference is not confounded by an interacting factor. In other words, the absence of a significant interaction between feeding group and another factor is important to confirm that any significant difference found between feeding groups is indeed attributable to the feeding group and not to the other factor. If an interaction is found with another factor, it is prudent to break the data down and analyze it separately for each subpopulation of the interacting factor.

TABLE 1

Parameters, Estimated Weights and Fit measures for Subject No. 1802

| Target Visit Age - days (weeks) GAA | Actual Visit Age (days GAA) | Measured Weight (g) | Est. Weight[1] (g) at Target (Stage 1) | Est. Weight[2] (g) at Target (Stage 2) | Sum of Squares Error vs. Measured |
|---|---|---|---|---|---|
| −7 (−1) | −77 | 1124 | 988 | 966 | |
| 0 (0) | −23 | 2280 | 2304 | 2300 | |
| +7 (+1) | 7 | 3180 | 3139 | 3148 | |
| +28 (+4) | 37 | 4027 | 3954 | 3973 | |
| +56 (+8) | 60 | 4645 | 4531 | 4554 | |
| +84 (+12) | 100 | 5305 | 5396 | 5421 | |
| +112 (+16) | | | | | 64973.73[1] |
| +168 (+24) | 183 | 6785 | n/a | 6619 | |
| +252 (+36) | 240 | 6965 | n/a | 7079 | |
| +365 (+52) | — | — | — | — | |
| | | | | | 107437.92[2] |

[1]Values determined for the parameters a, b, and c by this process in Stage 1 (through 84 days GAA) are: a = 2943.81, b = 0.97075, and c = 0.009789.
[2]Values determined for the parameters a, b, and c by this process in Stage 2 (through 252 days GAA) are: a = 2949.73, b = 0.96276, and c = 0.009999.

In Stage 1, the curve was fitted to available data through 16 weeks and this produced one set of parameters (see note 1) and one set of estimated weights for the common target times (4$^{th}$ column). In Stage 2, the same infants are followed to 52 weeks GAA and a second curve was fitted to all the data, generating a second set of parameters and a second set of estimated weights (5$^{th}$ column). Also given in Table 1 are the measured weights at the time (GAA) of actual visit. The first sum of the squares error is calculated using the difference between the actual data and the estimated data using the first parameter set and function (4$^{th}$ column). The second sum of the squares error is calculated using the difference between the actual data and the estimated data using the second parameter set and function (5$^{th}$ column), summed over all the data given in the table. An examination of the parameter values and estimated weight data from the functions fitted at Stage 1 and Stage 2 reveals them to be in good agreement.

In the comparison steps, both the raw data and data estimated using the fitted functions were used to test for associations between:
1. the subject weight, subject length, and subject head circumference; and
2. each of the following factors: feeding group (SWI or NEO), the birthweight group (<1250 grams=VLBW or ≧1250 grams=LBW), the sex (M or F), the visit time, or the site (sites A, B, C D or E), and each of the following interactions of factors: feeding group with sex, feeding group with birthweight group, and feeding group with visit time.

In the world of statisticians and SAS programs, an interaction of two factors is represented using a "*" operator.

As is well known to statisticians, a p-value is a measure of the probability that an observation made is due to chance. It is used as a tool to assess the confidence with which an observation is said to be true or a difference is said to exist. By convention, if the probability of a chance occurrence is less than 5% ($p<0.05$), the observation is said to be true or the difference is said to exist. In hypothesis testing, the null hypothesis of "no difference" between two groups A and B (A=B, in shorthand notation) is posed and tested. If there are two possible alternative outcomes (e.g. A>B and A<B are both of concern) then a two-sided p-value is used whereby the probability of error or chance result is allocated between the two outcomes. If there is just one alternative outcome of concern (A>B or A<B) then a one-sided p-value may be used, wherein all the potential error is on one side. The study design will indicate the proper test to employ. A p-value may or may not also be adjusted for multiple analyses or multiplicity of endpoints. Adjusting for this requires allocating the total error among each analysis or endpoint.

Part B—Comparative Analysis

The process described in part A was carried out for the measured weights of infants and the resulting p-values for the raw and estimated data are shown in Table 2Ai for Stage 1 (through 16 weeks) and in Table 2Aii for Stage 2 (through 52 weeks). The two-sided p-values were taken directly from the SAS output, and halved where the protocol specified a one-sided hypothesis design. Values in bold indicate significant differences.

TABLE 2Ai

Tests of Fixed Effects by Source of Variation for Weight for Stage 1

| Source of Variation | Reported Weight (n = 96) | Estimated Weight (n = 96) |
|---|---|---|
| Feeding Group | p = 0.0056 | p = 0.0916 <br> (p = 0.0458 one sided) |
| Site | p = 0.0001 | p = 0.0001 |
| Visit | p = 0.0001 | p = 0.0001 |
| Sex | p = 0.1703 | p = 0.2136 |
| Birthweight Group | p = 0.6360 | p = 0.9537 |
| Feeding Group * Visit | p = 0.0226 | p = 0.3118 |
| Feeding Group * Sex | p = 0.7782 | p = 0.4289 |
| Feeding Group * Birthweight Group | p = 0.9228 | p = 0.9144 |

TABLE 2Aii

Tests of Fixed Effects by Source of Variation for Weight for Stage 2

| Source of Variation | Reported Weight (N = 94) | Estimated Weights (N = 94) |
|---|---|---|
| Feeding Group | p = 0.0836 <br> (p = 0.0418 one-sided) | p = 0.0878 <br> (p = 0.0439 one-sided) |
| Site | p = 0.0141 | p = 0.0107 |
| Visit | p = 0.0001 | p = 0.0001 |
| Sex | p = 0.0001 | p = 0.0001 |
| Birthweight Group | p = 0.0111 | p = 0.0063 |
| Feeding Group * Visit | p = 0.1970 | p = 0.6007 |
| Feeding Group * Sex | p = 0.3085 | p = 0.1957 |
| Feeding Group * Birthweight Group | p = 0.0660 | p = 0.0821 |

The apparently significant interaction of feeding group*visit (p=0.00226) found in Stage 1 (Table 2Ai) reported weights suggests that the two assigned formulas had differing effects on weight as the infants aged; either subjects grew differently on the two feedings or the timing of visits was an important factor. This interaction does not appear to be significant using the full data set of Stage 2 (Table 2Aii). Importantly, the significance of this interaction "disappears" even in Stage 1 when using the estimated data for the analysis. This suggests that the mis-timing of visits did play a significant role and confirms the utility of the invention; the apparently significant interaction was merely due to there having been a happenstance tendency for infants in one feeding group to have been brought in either earlier or later than infants in the other feeding group. Over the course of time during Stage 2, this happenstance event evened out and became not significant, as might be predicted using the estimated data at Stage 1.

The use of estimated outcome data reduced the amount of "noise" in the data also. Table 3A gives average reported and estimated weights for the two feeding groups is through Stage 2. At both Stage 1 and Stage 2 the standard errors in weight were consistently lower when estimated outcome data were used, although this effect was more pronounced during Stage 1 than Stage 2. This shows that use of the size modeling function reduced or eliminated a source of variation in the data, leading to a "fairer" comparison of the two feeding groups.

TABLE 3A

Least Squares Means ± SEM for Reported and Estimated Weight by Visit*

| Visit | Feeding Group | Reported Weight (gm) | Estimated Weight (gm) |
|---|---|---|---|
| Overall | NeoSure | 5593 ± 88 | 5544 ± 87 |
| | Similac with Iron | 5389 ± 88 | 5348 ± 86 |
| Study Day 1 | NeoSure | 2147 ± 115 | 2268 ± 108 |
| | Similac with Iron | 2177 ± 118 | 2229 ± 110 |
| Term | NeoSure | 3124 ± 110 | 3212 ± 105 |
| | Similac with Iron | 3025 ± 111 | 3053 ± 104 |
| Term + 4 (weeks) | NeoSure | 4235 ± 111 | 4033 ± 105 |
| | Similac with Iron | 3896 ± 112 | 3836 ± 104 |
| Term + 8 | NeoSure | 4959 ± 116 | 4820 ± 106 |
| | Similac with Iron | 4730 ± 114 | 4586 ± 105 |
| Term + 12 | NeoSure | 5716 ± 114 | 5558 ± 107 |
| | Similac with Iron | 5437 ± 113 | 5325 ± 106 |
| Tenn + 24 | NeoSure | 7232 ± 118 | 7252 ± 110 |
| | Similac with Iron | 6873 ± 118 | 6894 ± 110 |
| Term + 36 | NeoSure | 8112 ± 118 | 8199 ± 112 |
| | Similac with Iron | 8012 ± 123 | 7995 ± 114 |
| Term + 52 | NeoSure | 9218 ± 131 | 9010 ± 122 |
| | Similac with Iron | 8961 ± 130 | 8866 ± 120 |

*Controlling for other factors in the model

Based on these results, we can infer that the infants who were fed NeoSure experienced significantly greater growth as measured by weight than those fed Similac With Iron.

The process described in part A was carried out for the measured lengths of infants and the resulting p-values for the raw and estimated data are shown in Tables 2Bi and 2Bii. The two-sided p-values were taken directly from the SAS output, and halved where the protocol specified a one-sided design. Values in bold indicate significant differences.

TABLE 2Bi

Tests of Fixed Effects by Source of Variation for Length for Stage 1

| Source of Variation | Reported Length (n = 83) | Estimated Length (n = 83) |
|---|---|---|
| Feeding Group | p = 0.0010 <br> (p = 0.0005 one sided) | p = 0.0118 <br> (p = 0.0059 one sided) |
| Site | p = 0.0001 | p = 0.0001 |
| Visit | p = 0.0001 | p = 0.0001 |
| Sex | p = 0.3551 | p = 0.7876 |
| Birthweight Group | p = 0.0001 | p = 0.0001 |
| Feeding Group * Visit | p = 0.2350 | p = 0.6035 |
| Feeding Group * Sex | p = 0.7552 | p = 0.2497 |
| Feeding Group * Birthweight Group | p = 0.4621 | p = 0.7933 |

TABLE 2Bii

Tests of Fixed Effects by Source of Variation for Length for Stage 2

| Source of Variation | Reported Length (N = 89) | Estimated Length (N = 89) |
|---|---|---|
| Feeding Group | p = 0.0085 <br> (p = 0.0043 one-sided) | p = 0.0156 <br> (p = 0.0078 one-sided) |
| Site | p = 0.0001 | p = 0.0001 |
| Visit | p = 0.0001 | p = 0.0001 |
| Sex | p = 0.0018 | p = 0.0033 |

TABLE 2Bii-continued

Tests of Fixed Effects by Source of Variation for Length for Stage 2

| Source of Variation | Reported Length (N = 89) | Estimated Length (N = 89) |
|---|---|---|
| Birthweight Group | p = 0.0008 | p = 0.0005 |
| Feeding Group * Visit | p = 0.4512 | p = 0.0616 |
| Feeding Group * Sex | p = 0.7655 | p = 0.5026 |
| Feeding Group * Birthweight Group | p = 0.0604 | p = 0.0906 |

The differences in Stage 1 vs. Stage 2 tests for fixed effects for length are unremarkable. No interactions were found to be significant for any of the data. The one-sided p-values of 0.0059 (Stage 1) and 0.0078 (Stage 2) for feeding group effect (NEO>SWI) for estimated length correspond to the one-sided null hypothesis stated in the protocol, and support the claim that infants grew longer on NEO than on SWI. This is confirmed by the least squares means data (see Table 3B) which show that, through Stage 2, infants fed NEO grew to longer mean lengths than the infants on SWI. This effect was also observed to be significant after Stage 1.

TABLE 3B

Least Squares Means ± SEM for Reported and Estimated Length by Visit*

| Visit | Feeding Group | Reported Length (cm) | Estimated Length (cm) |
|---|---|---|---|
| Overall | NeoSure | 58.8 ± 0.3 | 57.7 ± 0.3 |
|  | Similac with Iron | 57.8 ± 0.3 | 58.5 ± 0.3 |
| Study Day 1 | NeoSure | 44.5 ± 0.4 | 44.6 ± 0.4 |
|  | Similac with Iron | 44.3 ± 0.4 | 44.6 ± 0.3 |
| Term | NeoSure | 48.2 ± 0.4 | 48.8 ± 0.4 |
|  | Similac with Iron | 47.4 ± 0.4 | 47.9 ± 0.3 |
| Term + 4 | NeoSure | 52.6 ± 0.4 | 52.3 ± 0.4 |
|  | Similac with Iron | 51.7 ± 0.4 | 51.3 ± 0.3 |
| Term + 8 | NeoSure | 56.0 ± 0.4 | 55.5 ± 0.4 |
|  | Similac with Iron | 55.1 ± 0.4 | 54.4 ± 0.3 |
| Term + 12 | NeoSure | 59.3 ± 0.4 | 58.4 ± 0.4 |
|  | Similac with Iron | 57.9 ± 0.4 | 57.4 ± 0.3 |
| Term + 24 | NeoSure | 65.5 ± 0.4 | 65.4 ± 0.4 |
|  | Similac with Iron | 63.8 ± 0.4 | 63.9 ± 0.3 |
| Term + 36 | NeoSure | 69.9 ± 0.4 | 70.1 ± 0.4 |
|  | Similac with Iron | 69.1 ± 0.4 | 68.9 ± 0.4 |
| Term + 52 | NeoSure | 74.7 ± 0.5 | 74.3 ± 0.4 |
|  | Similac with Iron | 73.5 ± 0.4 | 73.4 ± 0.4 |

*Controlling for other factors in the model

The process described in part A was carried out for the measured head circumference of infants and the resulting p-values for the raw and estimated data are shown in Tables 2Ci and 2Cii. The two-sided p-values were taken directly from the SAS output. Values in bold indicate significant differences.

TABLE 2Ci

Tests of Fixed Effects by Source of Variation for Head Circumference for Stage 1

| Source of Variation | Reported Head Circumference (n = 98) | Estimated Head Circumference (n = 98) |
|---|---|---|
| Feeding Group | p = 0.2280 | p = 0.5914 |
| Site | p = 0.0001 | p = 0.0001 |
| Visit | p = 0.0001 | p = 0.0001 |
| Sex | p = 0.0002 | p = 0.0022 |
| Birthweight Group | p = 0.0182 | p = 0.0235 |

TABLE 2Ci-continued

Tests of Fixed Effects by Source of Variation for Head Circumference for Stage 1

| Source of Variation | Reported Head Circumference (n = 98) | Estimated Head Circumference (n = 98) |
|---|---|---|
| Feeding Group * Visit | p = 0.0002 | p = 0.8610 |
| Feeding Group * Sex | p = 0.9210 | p = 0.8829 |
| Feeding Group * Birthweight Group | p = 0.0032 | p = 0.0085 |

TABLE 2Cii

Tests of Fixed Effects by Source of Variation for Head Circumference for Stage 2

| Source of Variation | Reported Head Circumference (N = 95) | Estimated Head Circumference (N = 95) |
|---|---|---|
| Feeding Group | p = 0.2283 | p = 0.3613 |
| Site | p = 0.0001 | p = 0.0001 |
| Visit | p = 0.0001 | p = 0.0001 |
| Sex | p = 0.0001 | p = 0.0001 |
| Birthweight Group | p = 0.0004 | p = 0.0006 |
| Feeding Group * Visit | p = 0.0211 | p = 0.3704 |
| Feeding Group * Sex | p = 0.6485 | p = 0.4732 |
| Feeding Group * Birthweight Group | p = 0.0021 | p = 0.0029 |

Follow up of the significant interaction (p=0.0002 at Stage 1; p=0.0211 at Stage 2) between feeding group and visit for the reported measures produces a very enlightening result. The complete data set, through Stage 2, indicated a differential feeding effect at only one time point, the +24 week visit (NEO>SWI, p=0.0108, one-sided, see Table 3Ci). But here again the apparently significant interaction of feeding group visit "disappears" when the estimated data through Stage 2 is analyzed in accordance with the invention (Table 3Ci).

TABLE 3Ci

Least Squares Means ± SEM for Reported and Estimated Head Circumference by Visit*

| Visit | Feeding Group | Reported Head Circumference (cm) | Estimated Head Circumference (cm) |
|---|---|---|---|
| Overall | NeoSure | 39.5 ± 0.2 | 39.4 ± 0.2 |
|  | Similac with Iron | 39.3 ± 0.2 | 39.2 ± 0.2 |
| Study Day 1 | NeoSure | 31.5 ± 0.2 | 31.6 ± 0.2 |
|  | Similac with Iron | 32.1 ± 0.2 | 31.8 ± 0.2 |
| Term | NeoSure | 34.7 ± 0.2 | 34.6 ± 0.2 |
|  | Similac with Iron | 34.5 ± 0.2 | 34.4 ± 0.2 |
| Term + 4 | NeoSure | 37.2 ± 0.2 | 36.8 ± 0.2 |
|  | Similac with Iron | 36.8 ± 0.2 | 36.6 ± 0.2 |
| Term + 8 | NeoSure | 38.7 ± 0.2 | 38.7 ± 0.2 |
|  | Similac with Iron | 38.5 ± 0.2 | 38.4 ± 0.2 |
| Term + 12 | NeoSure | 40.2 ± 0.2 | 40.2 ± 0.2 |
|  | Similac with Iron | 39.9 ± 0.2 | 39.9 ± 0.2 |
| Term + 24 | NeoSure | 43.2 ± 0.2[a] | 43.2 ± 0.2 |
|  | Similac with Iron | 42.5 ± 0.2[a] | 42.8 ± 0.2 |
| Term + 36 | NeoSure | 44.5 ± 0.2 | 44.7 ± 0.2 |
|  | Similac with Iron | 44.1 ± 0.2 | 44.4 ± 0.2 |
| Term + 52 | NeoSure | 45.8 ± 0.3 | 45.6 ± 0.2 |
|  | Similac with Iron | 45.6 ± 0.3 | 45.5 ± 0.2 |

*Controlling for other factors in the model
[a]One-sided p-value = 0.0108, unadjusted for multiple steps However, the same analysis based on Stage 1 data only (see Table 3Cii) reveals that one might have been mislead by the reported measures data, which shows significant differences between feeding groups at three distinct visit-time points (term, +4 and +12 weeks GAA). But by applying the process of the invention and conducting the statistical comparison on the estimated data, one finds no significant differences at any time point. This strongly suggests the value of the invention in reducing errors in interpreting growth data. It is especially useful to align and smooth out apparent interactions with visit that result from mis-timing of outcome data accumulation.

TABLE 3Cii

Least Squares Means ± SEM for Reported and Estimated Head Circumference by Visit*

| Visit | Feeding Group | Reported Head C. (cm) | Estimated Head C. (cm) |
|---|---|---|---|
| Overall | NeoSure | 36.5 ± 0.2 | 36.4 ± 0.2 |
|  | Similac with Iron | 36.3 ± 0.2 | 36.3 ± 0.2 |
| Study Day 1 | NeoSure | 31.4 ± 0.2 | 31.7 ± 0.2 |
|  | Similac with Iron | 31.9 ± 0.2 | 31.7 ± 0.2 |
| Term | NeoSure | 34.8 ± 0.2[a] | 34.9 ± 0.2 |
|  | Similac with Iron | 34.3 ± 0.2[a] | 34.7 ± 0.2 |
| Term + 4 | NeoSure | 37.3 ± 0.2[b] | 37.0 ± 0.2 |
|  | Similac with Iron | 36.7 ± 0.2[b] | 36.9 ± 0.2 |
| Term + 8 | NeoSure | 38.7 ± 0.2 | 38.7 ± 0.2 |
|  | Similac with Iron | 38.6 ± 0.2 | 38.6 ± 0.2 |
| Term + 12 | NeoSure | 40.4 ± 0.2[c] | 40.0 ± 0.2 |
|  | Similac with Iron | 39.9 ± 0.2[c] | 39.9 ± 0.2 |

*Controlling for other factors in the model
[a]unadjusted one-sided p-value = 0.0175
[b]unadjusted one-sided p-value = 0.0338
[c]unadjusted one-sided p-value = 0.0386

The significant interaction shown in Tables 2Ci and 2Cii (p=0.0032 at Stage 1 and p=0.0021 at Stage 2) between feeding group and birthweight group for the reported measures indicates differential feeding effects for the two birthweight groups (LBW/VLBW), which was also apparent during Stage 1 and does not disappear using the estimated data for either Stage. This suggests the existence of a true interaction that should be investigated further by breaking the data down into each birthweight group. Comparison of least squares means indicates that VLBW NEO-fed subjects grew to larger head circumferences than VLBW SWI-fed subjects (p=0.0026, one-sided, see Table 3Ciii), but there was no difference between feeding groups in the LBW group. The analysis using the estimated values from the growth model yields similar results (VLBW NEO >VLBW SWI, p=0.0042, one-sided, see Table 3Ciii).

TABLE 3C iii

Least Squares Means ± SEM for Reported and Estimated Head Circumference by Birthweight group*

| Birthweight Group | Feeding Group | Reported Head Circumference (cm) | Estimated Head Circumference (cm) |
|---|---|---|---|
| Low Birthweight ("LBW") | NeoSure | 39.6 ± 0.2 | 40.0 ± 0.2 |
|  | Similac with Iron | 40.0 ± 0.2 | 39.5 ± 0.2 |
| Very Low Birthweight ("VLBW") | NeoSure | 39.4 ± 0.2[b] | 39.3 ± 0.2[c] |
|  | Similac with Iron | 38.5 ± 0.2[b] | 38.5 ± 0.2[c] |

*Controlling for other factors in the model
[b]One-sided p-value = 0.0026, unadjusted for multiplicity
[c]One-sided p-value = 0.0042, unadjusted for multiplicity

We claim:

1. A method of interpreting results from a study, said method comprising the steps of:
   obtaining measured size data for each of two or more subjects regarding the subjects' sizes as a function of an independent variable, t, that corresponds to a measure of the subjects' ages, wherein t for at least one subject differs from t for at least one other subject;
   determining for each of the subjects a set of values for the three parameters a, b, and c of a three parameter size modeling function defined by $f_{a,b,c}(t) = a \exp(b(1-\exp(-ct)))$, to provide an optimal fit of the size modeling function to the data regarding the subject's size as a function of t;
   estimating for each of the subjects, using said size modeling function and said set of determined values for the parameters, sizes for the subject at a particular age, which particular age is the same for all of the subjects; and
   comparing the estimated sizes to interpret the study results.

2. A method as defined in claim 1 wherein the size measurement obtained is selected from the group consisting of weight, length and head circumference.

3. A method as defined in claim 1 wherein the function parameters are determined to obtain an optimal fit by means of minimizing the least squares error function.

4. A method as defined in claim 1 wherein the independent variable t is gestation-adjusted age.

5. A method as defined in claim 1 wherein the subject is an infant.

6. A method as defined in claim 5 wherein the subject is a preterm infant.

7. A method as defined in claim 1 wherein the measured size data is for a set of ages that varies significantly from subject to subject.

8. A method as defined in claim 1 wherein at least the step of determining a set of values for said parameters a, b, and c is carried out by a computer processing means.

9. A method of conducting a clinical growth study comprising the steps of:
   obtaining measured size data for each of two or more subjects regarding the subjects' sizes as a function of an independent variable, t, that corresponds to a measure of the subjects' ages, wherein t for at least one subject differs from t for at least one other subject;
   determining for each of the subjects a set of values for the three parameters a, b, and c of a three parameter size modeling function defined by $f_{a,b,c}(t) = a \exp(b(1-\exp(-ct)))$, to provide an optimal fit of the size modeling function to the data regarding the subject's size as a function of t;
   estimating for each of the subjects, using said size modeling function and said set of determined values for the parameters, sizes for the subject at a particular age, which particular age is the same for all of the subjects; and
   comparing the estimated sizes to interpret the growth study results.

10. A method as defined in claim 9 wherein the growth variable to be measured is selected from the group consisting of weight, length and head circumference.

11. A device comprising:
   memory means encoded with or adapted to receive instructions, said instructions capable of directing a computer provided with measured outcome data regarding a subject size as a function of an age, t, to calculate values for three parameters, a, b, and, c of a three parameter subject size modeling function defined by $f_{a,b,c}(t) = a \exp(b(1-\exp(-ct)))$; such that the size modeling function with the calculated parameter values gives an optimal fit of the function to the data;

instructions to use the calculated values for parameters a, b, and c in the size modeling function to generate estimated data for each subject at a common predetermined age that is different from t for at least one subject; and output means for presenting the estimated data.

12. A device as defined in claim 11 further including instructions to calculate values for parameters a, b, and c such that the optimal fit is a least squares fit.

13. A device as defined in claim 11 further including instructions to perform comparisons using estimated data for each subject.

14. A method of processing data for improved interpretation, said method comprising the steps of:

obtaining measured outcome data for a plurality of test subjects at times, $t_i$, corresponding to a measure of time, wherein $t_i$ for at least one subject differs from $t_i$ for at least one other subject;

determining for each subject a set of values for the three parameters a, b, and c of a three parameter modeling function defined by $f_{a,b,c}(t) = a \exp(b(1-\exp(-ct)))$ that relate outcome data to an independent time variable t, to provide an optimal fit of the modeling function to the measured outcome data for each subject over all $t_i$;

estimating outcome data for at least one of the subjects, using said modeling function and said the determined set of parameter values, for a particular time that is different from $t_i$ at which the outcome data was measured; and comparing the estimated outcome data from the at least one subject with estimated or measured outcome data from at least one other subject to interpret the results.

15. A method as defined in claim 14 wherein the particular time that is different from $t_i$ at which the outcome was measured is the same for all of the subjects.

16. A method as defined in claim 14 wherein estimated outcome data is estimated for a plurality of subjects.

17. A method as defined in claim 14 wherein the independent time variable, t, is gestation-adjusted age.

18. A method as defined in claim 14 wherein the subject is an infant.

19. A method as defined in claim 18 wherein the outcome data is selected from the group consisting of weight, length and head circumference of the subject.

20. A method as defined in claim 14 wherein the outcome data is a measurement of growth.

* * * * *